United States Patent
Reuter et al.

(10) Patent No.: US 9,253,988 B2
(45) Date of Patent: *Feb. 9, 2016

(54) **PROCESS FOR INHIBITING *CLOSTRIDIUM* MICROORGANISMS**

(71) Applicant: Osprey Biotechnics, Inc., Sarasota, FL (US)

(72) Inventors: Christopher J. Reuter, Parrish, FL (US); Steven J. MacKenzie, Sarasota, FL (US); Lauren G. Danielson, Bradenton, FL (US); Vincent Scuilla, Sarasota, FL (US)

(73) Assignee: Osprey Biotechnics, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/209,271

(22) Filed: Mar. 13, 2014

(65) Prior Publication Data

US 2015/0257390 A1    Sep. 17, 2015

(51) Int. Cl.
*A62D 3/00* (2007.01)
*A01N 63/00* (2006.01)
*C12R 1/10* (2006.01)

(52) U.S. Cl.
CPC ... *A01N 63/00* (2013.01); *A62D 3/00* (2013.01); *C12R 1/10* (2013.01)

(58) Field of Classification Search
CPC ............ A01N 63/00; C12R 1/10; A62D 3/02
See application file for complete search history.

(56) References Cited

U.S. PATENT DOCUMENTS

| | | | |
|---|---|---|---|
| 6,025,187 A | * | 2/2000 | Penaud ................. 435/262.5 |
| 6,291,426 B1 | | 9/2001 | Heins et al. |
| 8,236,549 B2 | | 8/2012 | Kang et al. |
| 8,338,160 B2 | | 12/2012 | Tzeng et al. |
| 8,377,455 B2 | | 2/2013 | Ceri et al. |
| 8,404,476 B2 | | 3/2013 | Fernandez Martinez et al. |

FOREIGN PATENT DOCUMENTS

CN        103243041 A    *    8/2013

OTHER PUBLICATIONS

STN abstract for CN 103243014 (publication date Aug. 14, 2013) dowloaded from CAPLUS database Apr. 5, 2015.*
Wentz, M. Science (1967) 155: 89-90.*
Machine translation of CN 103243041 A published Aug. 14, 2013.*

* cited by examiner

*Primary Examiner* — Susan Hanley
(74) *Attorney, Agent, or Firm* — Butzel Long

(57) ABSTRACT

The invention relates to the use of *Bacillus licheniformis* strain OBT618 (ATCC PTA-122188) for inhibiting *Clostridium* pathogens in a material such as water or manure contaminated with the pathogen. The strain can be added to drinking water, animal feed or animal litter to reduce disease caused by the presence of *Clostridium* in an animal.

5 Claims, 2 Drawing Sheets

B licheniformos-OBT618-16S-rRNA-seq fasta
>B.licheniformos OBT618
TGGAGAGTTTGATCCTGGCTCAGGACGAACGCTGGCGGCGTGCCTAATACATGCAAGTCGAGCGGACCGACGGGAGCTTGCTCC
CTTAGGTCAGCGGCGGACGGGTGAGTAACACGTGGGTAACCTGCCTGTAAGACTGGGATAACTCCGGGAAACCGGGGCTAATAC
CGGATRCTTGATTGAACCGCATGGTTCAATTATAAAAGGTGGCTTTTAGCTACCACTTACAGATGGACCCGCGGCGCATTAGCT
AGTTGGTGAGGTAACGGCTCACCAAGGCAACGATGCGTAGCCGACCTGAGAGGGTGATCGGCCACACTGGGACTGAGACACGGC
CCAGACTCCTACGGGAGGCAGCAGTAGGGAATCTTCCGCAATGGACGAAAGTCTGACGGAGCAACGCCGCGTGAGTGATGAAGG
TTTTCGGATCGTAAAACTCTGTTGTTAGGGAAGAACAAGTACCGTTCGAATAGGGCGGTACCTTGACGGTACCTAACCAGAAAG
CCACGGCTAACTACGTGCCAGCAGCCGCGGTA

FIGURE 1

SEQUENCE LISTING

```
<160> NUMBER OF SEQ ID NOS: 1

<210> SEQ ID NO 1
<211> LENGTH: 536
<212> TYPE: DNA
<213> ORGANISM: Bacillus licheniformis

<400> SEQUENCE: 1
tggagagttt gatcctggct caggacgaac gctggcggcg tgcctaatac atgcaagtcg      60
agcggaccga cgggagcttg ctcccttagg tcagcggcg acgggtgagt aacacgtggg     120
taacctgcct gtaagactgg gataactccg ggaaaccggg gctaataccg gatrcttgat     180
tgaaccgcat ggttcaatta taaaaggtgg cttttagcta ccacttacag atggacccgc     240
ggcgcattag ctagttggtg aggtaacggc tcaccaaggc aacgatgcgt agccgacctg     300
agagggtgat cggccacact gggactgaga cacggcccag actcctacgg gaggcagcag     360
tagggaatct tccgcaatgg acgaaagtct gacggagcaa cgccgcgtga gtgatgaagg     420
ttttcggatc gtaaaactct gttgttaggg aagaacaagt accgttcgaa tagggcggta     480
ccttgacggt acctaaccag aaagccacgg ctaactacgt gccagcagcc gcggta         536
```

PROCESS FOR INHIBITING *CLOSTRIDIUM* MICROORGANISMS

CROSS-REFERENCE TO RELATED APPLICATIONS

Not Applicable.

FIELD OF THE DISCLOSURE

This disclosure concerns the use of a novel strain of *Bacillus licheniformis* for improving safety and reducing incidents of disease in humans and animals.

BACKGROUND OF THE DISCLOSURE

*Bacillus licheniformis* bacterium is a gram-positive, mesophilic bacterium that is commonly found in the soil and on bird feathers, especially on the chest and back plumage of ground-dwelling and aquatic birds. It is cultured to obtain protease for use in laundry detergent. Other applications that have been explored include use in synthesis of gold nanoparticles and as an agent to fight tooth decay.

*Clostridium* is a gram positive bacterium capable of forming spores and colonizing the intestines of humans and animals of agricultural importance such as cattle, poultry, and swine. There are a variety of *Clostridium* species that are troublesome pathogens in both humans and animals. Not only do the bacteria themselves present problems in terms of their pathogenicity, they also produce toxins that can cause extreme health effects in humans and animals. In humans, the *Clostridium* bacteria from the species *botulinum* produces the botulism toxin that can cause muscle paralysis; the *perfringens* species causes food poisoning and gas gangrene in people and enterotoxaemia in sheep and goats; the *tetani* species causes tetanus, resulting in lockjaw or spastic paralysis in humans, cattle, dogs and other animals; the *sordelli* species causes pneumonia, endocarditis, arthritis, peritonitis and myonecrosis, as well as toxic shock syndrome.

The *difficile* species is of concern to human and animals for colitis. It is capable of colonizing the intestines of humans and animals, including horses, cattle, poultry and swine. Much foodborne illness is also linked to *C. difficile*. In humans, *C. difficile* is most commonly known for its ability to cause disease in hospitalized patients who are being treated with antibiotics or chemotherapy for an infection from another bacterium. During this time, exposure to *C. difficile*, which is resistant to many common antibiotics, takes advantage of the reduction of colonic flora, growing rapidly and causing severe diarrhea, bloating, and abdominal pain.

Many cases of *C. difficile* infection have been reported from non-hospitalized patients where the source is believed to be mainly foodborne illness. *C. difficile* has been isolated from animal fecal samples of agricultural importance such as cattle, poultry, and swine and also from food products which come from these produce. This link is believed to be the source of many cases of foodborne illness.

Accordingly, new and effective methods to inhibit *C. difficile* and other *Clostridium* species, along with new and effective methods to prevent them from producing the harmful toxins are desired.

SUMMARY OF THE DISCLOSURE

The novel strain of *Bacillus licheniformis* (strain OBT618) has utility in various processes that improve food safety and decontaminate water, food processing equipment, holding pens, manure, treating ponds, farm runoff, aquaculture facilities, and the like, and thereby reduce incidents of disease in animals and humans.

The processes generally involve contacting liquid, solid or semi-solid materials contaminated with a pathogenic microorganism with an amount of *Bacillus licheniformis* strain OBT618 that is effective to have an inhibitory effect on the pathogenic microorganism.

BRIEF DESCRIPTION OF THE DRAWING

FIG. 1 (SEQ ID NO: 1) is the relevant sequence for *Bacillus licheniformis* strain OBT618.

DETAILED DESCRIPTION

Figure 2:
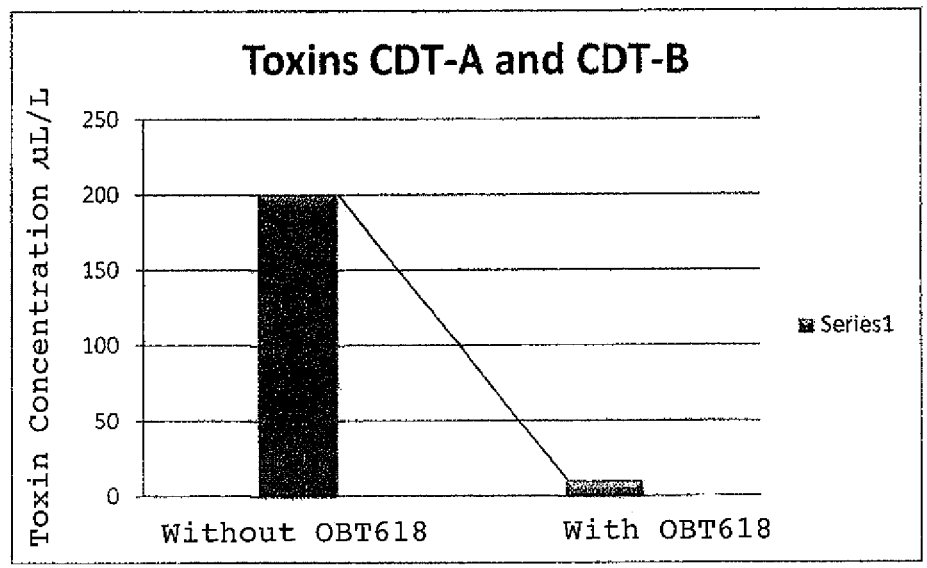
FIG. 2 is a graph illustrating Toxin CDT-A and CDT-B concentration of two *Clostridium* cultures that are identical except for the addition of OBT618 to one of the samples.

It has been discovered that the novel *Bacillus licheniformis* strain OBT618 exhibits an inhibitory effect on pathogens of *Clostridium* and has many applications that can improve safety and reduce incidents of disease in humans and animals.

The term "inhibit" means to reduce or arrest growth and/or reproduction of *Clostridium* species, and/or to reduce or arrest production by and/or secretion of toxins from *Clostridium*. The term "inhibit" also encompasses killing *Clostridium* species and/or reducing or arresting the pathogenic or toxic effects of *Clostridium* species.

The term "effective amount" means an amount that will achieve a desired inhibitory effect to reduce incidents of diseases caused by pathogens of *Clostridium*. Effective amounts for particular applications can be determined by routine experimentation.

Disclosed is a novel strain of bacterium that produces specific types of useful enzymes, metabolites and antibiotics to inhibit both the growth and toxin production from *Clostridium* species. These enzymes, metabolites and antibiotics reduce the potential for illness and disease by using the OBT618 bacterium.

Wastewater contaminated with *C. difficile* can be treated with the novel OBT618 by spraying, direct inoculation of a liquid or a powder or a block containing the bacteria to reduce the *C. difficile* contamination and to reduce the toxin production from the *C. difficile* or other *Clostridium* species.

Lagoons, manure piles, or pens containing waste from pig, cattle, sheep, chicken and equine can be treated with the novel OBT618 by spraying or dispersing in a powder form the bacteria to reduce the *C. difficile* contamination and to reduce the toxin production from the *C. difficile* or other *Clostridium* species.

Animal feed can be treated by using the novel OBT618 bacterium as a direct fed microbial to either mix with the feed or as a separate feed supplement to reduce intestinal *C. difficile* colitis outbreaks and to reduce internal toxin production by *Clostridium* species.

Animal water can be treated by using the novel OBT618 bacterium to reduce the abundance and spread of *C. difficile* in drinking water and to inoculate the animal's intestinal tract to reduce intestinal *C. difficile* colitis outbreaks and to reduce internal toxin production by *Clostridium* species.

Chicken litter or other animal litter can be treated by using the novel OBT618 bacterium to spray the litter to reduce intestinal *C. difficile* colitis outbreaks and to reduce internal toxin production by *Clostridium* species in the animal.

Meat processing or food processing facility waste can be treated with the novel OBT618 bacterium by spraying, direct inoculation of a liquid or a powder or a block containing the bacterium to reduce the *C. difficile* contamination and to reduce the toxin production from the *C. difficile* or other *Clostridium* species.

Farm ponds can be treated with the novel OBT618 by spraying, direct inoculation of a liquid or a powder or a block containing the bacteria to reduce the *C. difficile* contamination and to reduce the toxin production from the *C. difficile* or other *Clostridium* species.

The effect of adding OBT618 to a *Clostridium* culture producing CDT-A and CDT-B toxins is shown in FIG. 2. The addition of the *Bacillus licheniformis* strain OBT618 reduces CDT-A and CDT-B toxin production to a substantially lower level.

Figure 3:
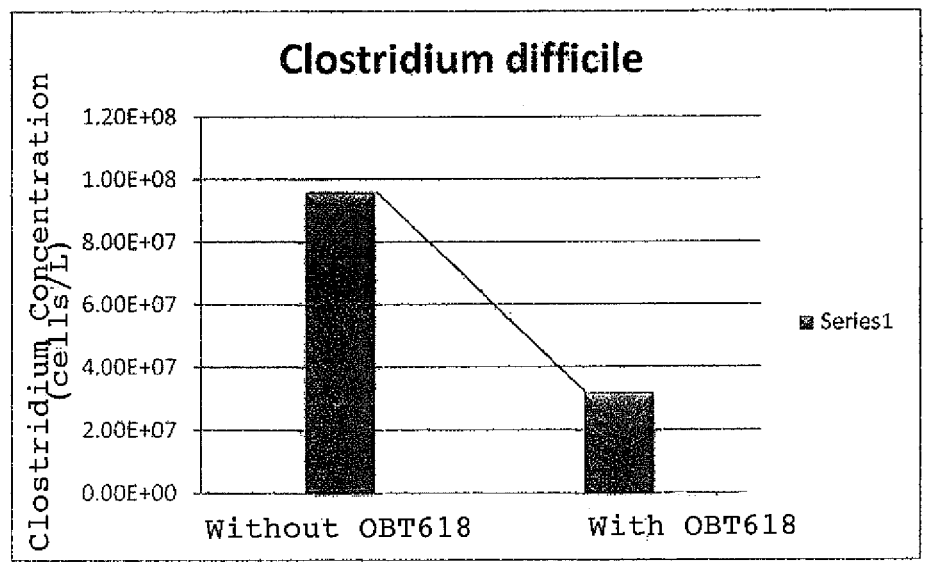
FIG. 3 is a graph illustrating bacteria populations or concentrations for two *Clostridium* cultures that are identical except for the addition of OBT618 to one of the two samples.

The effect of adding OBT618 to a *Clostridium* culture population is shown in FIG. 3. The addition of *Bacillus licheniformis* strain OBT618 profoundly reduces the *Clostridium* bacteria population.

The described embodiments are preferred and/or illustrated, but are not limiting. Various modifications are considered within the purview and scope of the appended claims.

The *Bacillus licheniformis* strain OBT618 was deposited under the Budapest Treaty and will be irrevocably and without restriction or condition released to the public upon issuance of a patent. The *Bacillus licheniformis* strain OBT 618 was deposited May 29, 2015 at the American Type Culture Collection (ATCC), P.O. Box 1549, Manassas, Va. 20108 and given accession number PTA-122188.

What is claimed is:

1. A method of inhibiting pathogens of *Clostridium* comprising:
    adding to a material contaminated with *Clostridium* an amount of *Bacillus licheniformis* strain OBT618 as deposited with the American Type Culture Collection under accession number PTA-122188 that is effective to exhibit an inhibitory effect on the *Clostridium*, wherein the *Bacillus licheniformis* strain OBT618 has the nucleotide sequence SEQ ID No. 1.

2. The method of claim 1, wherein the *Bacillus licheniformis* strain OBT618 is added to water contaminated with *Clostridium*.

3. The method of claim 1, wherein the *Bacillus licheniformis* strain OBT618 is added to manure contaminated with *Clostridium*.

4. A method of reducing disease caused by the presence of *Clostridium* in an animal by administering to an animal in need thereof an animal feed or drinking water comprising *Bacillus licheniformis* strain OBT618 as deposited with the American Type Culture Collection under accession number PTA-122188 in an amount that is effective to exhibit an inhibitory effect on the *Clostridium* nucleotide sequence SEQ ID No. 1.

5. A method of reducing disease caused by the presence of *Clostridium* in an animal by contacting an animal in need thereof with an animal litter comprising *Bacillus licheniformis* strain OBT618 as deposited with the American Type Culture Collection under accession number PTA-122188 that is effective to exhibit an inhibitory effect on the *Clostridium*, wherein the *Bacillus licheniformis* strain OBT618 has the nucleotide sequence SEQ ID No. 1.

* * * * *